(12) United States Patent
Tietz et al.

(10) Patent No.: US 8,957,249 B2
(45) Date of Patent: Feb. 17, 2015

(54) PROCESS FOR REMOVING, ISOLATING AND PURIFYING DICARBOXYLIC ACIDS

(75) Inventors: Wolfgang Tietz, Biendorf (DE); Joachim Schulze, Soest (DE)

(73) Assignee: Thyssenkrupp UHDE GmbH, Dortmund (DE)

( * ) Notice: Subject to any disclaimer, the term of this patent is extended or adjusted under 35 U.S.C. 154(b) by 146 days.

(21) Appl. No.: 13/806,904

(22) PCT Filed: May 31, 2011

(86) PCT No.: PCT/EP2011/002686
§ 371 (c)(1),
(2), (4) Date: Dec. 26, 2012

(87) PCT Pub. No.: WO2011/160760
PCT Pub. Date: Dec. 29, 2011

(65) Prior Publication Data
US 2013/0096343 A1    Apr. 18, 2013

(51) Int. Cl.
| | |
|---|---|
| C07C 51/42 | (2006.01) |
| C07C 51/00 | (2006.01) |
| C07C 51/43 | (2006.01) |
| C07B 63/00 | (2006.01) |
| C07C 51/47 | (2006.01) |
| C12P 7/44 | (2006.01) |
| C12P 7/46 | (2006.01) |

(52) U.S. Cl.
CPC ................ C07C 51/43 (2013.01); C07B 63/00 (2013.01); C07C 51/42 (2013.01); C07C 51/47 (2013.01); C12P 7/44 (2013.01); C12P 7/46 (2013.01)
USPC .......................................... 562/593; 562/513

(58) Field of Classification Search
CPC .......... C07C 51/42–51/50; C07C 55/02–55/21
See application file for complete search history.

(56) References Cited

U.S. PATENT DOCUMENTS

| | | | |
|---|---|---|---|
| 5,034,105 A | 7/1991 | Berglund et al. | |
| 5,143,834 A | 9/1992 | Glassner et al. | |
| 5,168,055 A | 12/1992 | Datta et al. | |
| 5,177,008 A * | 1/1993 | Kampen | 435/139 |
| 6,265,190 B1 | 7/2001 | Yedur et al. | |
| 6,291,708 B1 | 9/2001 | Cockrem | |
| 2006/0276674 A1* | 12/2006 | Kushiku et al. | 562/562 |
| 2009/0162892 A1 | 6/2009 | Pompejus et al. | |
| 2012/0289742 A1* | 11/2012 | Gerberding et al. | 562/580 |
| 2013/0023682 A1* | 1/2013 | Woods et al. | 554/8 |

FOREIGN PATENT DOCUMENTS

| | | |
|---|---|---|
| CN | 101186571 A | 5/2008 |
| DE | 69006555 | 8/1994 |
| DE | 69015019 | 7/1995 |
| DE | 69015233 | 8/1995 |
| DE | 19939630 | 3/2001 |
| DE | 69821951 | 12/2004 |
| DE | 102004026152 | 12/2005 |
| DE | 60028958 | 2/2007 |
| EP | 1669459 | 6/2006 |
| WO | 2010003534 | 1/2010 |

OTHER PUBLICATIONS

Lee et al., Biotechnol. Prog. 2004, 20, 179-192.*
International Search Report for PCT/EP2011/002686, English translation attached to original, Both completed by the European Patent Office on Sep. 12, 2011, All together 5 Pages.

* cited by examiner

*Primary Examiner* — Karl J Puttlitz
(74) *Attorney, Agent, or Firm* — Brooks Kushman P.C.

(57) ABSTRACT

A process for removing, isolating and purifying dicarboxylic acid from fermentation broths, which includes the following steps: 1) removal of the biomass and any solids present from the fermentation broth in two successive stages, 2) removal of the dicarboxylic acid solution from the biomass-free fermentation broth by simulated moving bed (SMB) chromatography, 3) fine purification of the dicarboxylic acid solution, 4) multistage evaporative concentration and crystallization, and 5) separation and drying of the crystals.

20 Claims, No Drawings

PROCESS FOR REMOVING, ISOLATING AND PURIFYING DICARBOXYLIC ACIDS

Succinic acid and its compounds are widely used for various applications in the food industry, pharmaceuticals, cosmetics and the textile industry. Increasingly, succinic acid is also being used as feedstock for producing polymers.

The important thing in the industrial use of succinic acid produced by means of fermenting carbohydrate-bearing substrates using different microorganisms is the economic feasibility and efficiency of separating and purifying succinic acid from these watery fermentation solutions that not only contain succinic acid or succinic acid salts but also other organic acids, additional by-products of the fermentation, microorganisms and their components, and also substrate residues.

The qualities of the succinic acid produced can be differentiated by division into a technical-grade quality with a succinic acid content of at least 97 wt. % and a polymer-grade succinic acid with a content of at least 99.5 wt. %.

A great many patents describe the recovery of succinic acid from fermentation solutions, including
extractive processes using extraction agents such as tributylamines, trialkylamines, olefins, various alcohols and aromatic hydrocarbons,
processes using calcium hydroxide and sulphuric acid, where gypsum is accumulated as a by-product,
processes using electrodialysis,
thermal methods such as fractionated distillation or thermally staged chromatography,
high-pressure extraction using $CO_2$,
membrane processes such as reverse osmosis and other filtration processes,
with coupling of these processes and supplementation by additional state-of-the-art steps also under discussion. Such processes are described, inter alia, in patent specifications DE 69821951 T2, DE 69015233 T2, DE 69015019 T2, DE 69006555 T2, DE 69015019, DE19939630C2, DE 60028958T2, and DE 10 2004 026152 A1.

The disadvantage of many processes is the addition of further process fluids of which the target product must be free and any traces of which in the target product may lead to reduced quality and limitations in the use of said product. Practical implementation of said processes is sometimes also highly intensive from a technical and energetic perspective.

The objective of the invention is to provide a process for separating, recovering and purifying dicarboxylic acids, such as succinic acid, from fermentation broths, the process ensuring high product purity and avoiding the familiar disadvantages of other processes.

According to the present invention, the objective is achieved by using a process for separating, recovering and purifying dicarboxylic acid from fermentation broths through the application of several processing stages, said process comprising the following steps,
a) Separation of the biomass and any solids that are present from the fermentation broth in two consecutive stages,
b) Separation of the dicarboxylic acid solution from the biomass-free fermentation broth by means of simulated moving-bed chromatography (SMB),
c) Fine purification of the dicarboxylic acid solution,
d) Multi-stage evaporation and crystallisation,
e) Separation and drying of the crystals.

The fermentation broth that contains the dicarboxylic acid in the form of ammonium succinate, if said dicarboxylic acid is succinic acid, biomass and components of the substrate, is fed continuously to a precoat filtration unit or a microfiltration unit. In doing so, the temperature and pH value correspond to the fermentation values as it has been ascertained that inactivating the biomass by increasing the temperature and lowering the pH value by adding acid speeds up autolysis of the biomass and more lysis products are given off into the fermentation broth. Also, the time between the fermentation being completed and the biomass being separated out must be kept as short as possible and not be more than 2 h, with it preferably being less than 1-2 h. The biomass concentration in the filtrate should not exceed 1 g/l. These process parameters have a positive effect on the quality of the end product.

The filtrate from the precoat or microfiltration unit is added to a single or dual-stage ultrafiltration unit in the second step, in which biomass residues, non-soluble solids and higher molecular compounds are separated out. Membranes with a cut-off of ≤10 kDa were determined to achieve the optimum between product quality and membrane flux rates. The temperature of the liquid fluids should be ≥30° C. due to the solubility coefficient of ammonium succinate in water. The brine is recycled to the precoat or microfiltration unit, or alternatively collected and used as a feedstock for the production of technical-grade dicarboxylic acid, and the permeate is sent for further treatment.

Dicarboxylic acid is contained in the ultrafiltration permeate in the form of its salt—in the case of succinic acid in the form of ammonium succinate. To convert it to dicarboxylic acid, concentrated sulphuric acid is added and mixed in, thus lowering the pH value of the solution to values between 2.2 and 2.4 and creating ammonium sulphate in a stoichiometric ratio. In order to avoid unwanted precipitation, this process step is carried out at temperatures of between 30° C. and 60° C., and preferably kept at a range between 30° C. and 40° C. This pre-purified solution is available for the separation and purification of the dicarboxylic acid.

Separation of the acidic ultrafiltration permeate takes place in a simulated moving-bed chromatography unit. This represents a particularly efficient variant of high-performance liquid chromatography in which the series of several separation columns connected via valves in an infinite loop creates a large number of theoretical trays, thus considerably improving the separation efficiency of the chromatography. Cation exchangers and anion exchangers are used as the stationary phase. After the solution has been fed in, the dicarboxylic acid is bound to the stationary phase and, once the undesired fractions of the solution have been repeatedly washed out of the system, it is eluted and discharged separately as an extract. Demineralised water and/or vapour condensate are used as the eluent. It has been demonstrated that more than 95% of the dicarboxylic acid contained in the ultrafiltration permeate can be recovered in the extract, the ratio between the ultrafiltration permeate and the eluent varying between 1:1 and 1:2.5 with the use of eight anion exchanger columns connected in an infinite loop. The extract contains only small amounts of ammonium sulphate, acetic acid and dyes from the fermentor broth. The raffinate that is washed out contains a maximum 1 g/l of dicarboxylic acid as well as the ammonium sulphate and companion salts from the fermentation, such as phosphates, nitrates and chlorides.

For the production of polymer-grade dicarboxylic acid, fine purification of the extract from the simulated moving-bed chromatography unit can optionally be carried out with membranes that have a cut-off of 100 to 400 Da. It has been demonstrated that nanofiltration with a cut-off of approximately 200 Da yields good quality results. The process is conducted in a manner that ensures the nanofiltration brine does not make up more than 10% of the total throughput. Besides dicarboxylic acid, the brine also contains acetic acid and dyes and can be added to the feedstock for the production of technical-grade dicarboxylic acid. The permeate is sent for downstream processing to polymer-grade dicarboxylic acid.

Depending on the quality of the feedstocks used for the fermentation and the fermentation process parameters, additional fine purification of the permeate from the upstream nanofiltration or the extract from the SMB chromatography may be carried out due to the dye and companion residues that are still present. In this case, fine purification by means of activated carbon filtration and/or ion exchangers is arranged downstream. Depending on the chemical analysis of the contaminants cation and/or anion exchangers may be used as the ion exchanger resins.

The dicarboxylic acid product—both technical and polymer grade—is prepared by evaporating the dicarboxylic acid solution and then crystallising it. In doing so, it has been established that the process parameters have a major effect on product quality.

In order to obtain a technical-grade quality with a dicarboxylic acid content of ≥97 wt. % it is sufficient if evaporation and crystallisation take place in a single pass through these multi-stage process steps. The solution is evaporated to a concentration of 30 to 50 wt. %. The temperature gradient to be applied for cooling the solution during crystallisation was found to be a key parameter for product quality. Therefore, cooling should take place in steps of 3-8° C./min. and preferably in steps of 3-5° C./min. The crystals produced are then removed from the mother liquor by separation and washed with warm water with a temperature of 40° C., with the mother liquor being recycled to upstream of the evaporation. The crystals are dried after separation.

In order to obtain a polymer-grade dicarboxylic acid with a content of ≥99.5 wt. %, it was found that the temperature should be in the range of 70° C. to 80° C. and the solution must be adjusted to a concentration of 50±5 wt. %. The temperature gradient during cooling of the solution was found to be key to the quality of the crystals. Therefore, cooling takes place in steps of 1° C. to 5° C./h. This produces polymer-grade crystals that are removed by separation and dried. The mother liquor can be recycled. If required, the crystals can be dissolved in demineralised water and/or vapour condensate after separation and the crystallisation and separation step repeated.

The dicarboxylic acid crystals are preferably removed by separation after crystallisation, the accumulating mother liquor being recycled to upstream of the evaporation and the crystals then dried.

The ultrafiltration and the nanofiltration brines can optionally be combined and used as a feedstock solution for the production of a technical-grade dicarboxylic acid. The dried crystals are prepared for further use.

It is an advantage to use the process in accordance with the invention for the purification of dicarboxylic acids selected from the group fumaric acid, maleic acid, adipic acid, itaconic acid, benzoic acid and others, in particular for succinic acid.

Example 1

A fermentor broth containing ammonium succinate was pre-purified by means of filtration in accordance with the description. After converting the ammonium salt to the acid form of the succinic acid, the solution was separated out into 5.7 l extract and 6.6 l raffinate in a simulated moving-bed chromatography unit with a total of eight separation columns each with a strongly acidic cation exchanger in an infinite loop. With a permeate/eluent ratio of 2.4 the succinic acid recovery coefficient was 99.9%. The sulphate concentration in the extract was 238 mg/l and in the raffinate 35,709 mg/l, thus achieving a sulphate elimination of 99.4%.

Example 2

A fermentor broth containing ammonium succinate was pre-purified by means of filtration in accordance with the description. After converting the ammonium salt to the acid form of the succinic acid, the solution was separated out into 5.3 l extract and 6.1 l raffinate in a simulated moving-bed chromatography unit with a total of eight separation columns each with a strongly acidic cation exchanger in an infinite loop. With a permeate/eluent ratio of 2.2 the succinic acid recovery coefficient was 99.8%. A sulphate elimination of 97.9% was achieved.

Example 3

A succinic acid-containing extract from the simulated moving-bed chromatography unit was subjected to fine purification by means of nanofiltration with a cut-off of 200 Da. Contents of 44.8 g/l succinic acid and 698 mg/l sulphate were analysed in the extract. The filtered extract was crystallised and analysed. The crystals had a succinic acid content of 1.031 g/l, a residual sulphate content of 21.9 mg/l and a chloride content of 13.8 mg/l. The crystals were "white" in colour.

Example 4

A succinic acid-containing extract from the simulated moving-bed chromatography unit containing 44.77 g/l succinic acid and 699 mg/l sulphates was subjected to fine purification by means of nanofiltration with a cut-off of 200 Da and subsequent activated carbon filtration. The crystals produced after the fine purification contained 1,065 g/l succinic acid and 35.3 mg/l residual sulphates as well as 9.5 mg/l chlorides. The crystals were "pure white" in colour.

Example 5

A succinic acid-containing extract from the simulated moving-bed chromatography unit was subjected to fine purification by means of ion exchange. The extract contained 44.8 g/l succinic acid, 699 mg/l sulphates and 1.88 mg/l chlorides. The crystals produced from the fine-purified solution contained 967 g/l succinic acid, 37.6 mg/l sulphates and 0.92 mg/l chlorides. The crystals were "white" in colour.

The invention claimed is:

1. A process for separating, recovering, and purifying dicarboxylic acids from a fermentation broth containing biomass, comprising the following steps:
   a) separating biomass from a dicarboxylic acid moiety-containing fermentation broth in at least two steps, by
      a)1) continuously separating coarse biomass components from the fermentation broth to produce a liquid dicarboxylic acid moiety-containing separation stream having a biomass concentration of 1 g/l or less;
      a)2) feeding the separation stream from step a)1) to an ultrafiltration unit from which biomass residues, non-soluble solids, and high molecular weight compounds are separated, forming a permeate,
   wherein prior to step a)1) the temperature and pH of the fermentation broth correspond to the temperature and pH used during fermentation of the formation broth;

b) lowering the pH of the permeate from step a)2) to convert dicarboxylic acid salts contained in the permeate to free dicarboxylic acid, forming an acidified permeate;
c) separating dicarboxylic acid from the acidified permeate by
 c)1) passing the acidified permeate through a simulated moving-bed chromatography unit containing ion exchangers as a stationary phase, and binding the dicarboxylic acid to the stationary phase; and
 c)2) eluting bound dicarboxylic acid from the stationary phase to form a dicarboxylic acid-containing extract;
d) purifying the dicarboxylic acid-containing extract from step c)2) by a nanofiltration to form a nanofiltered permeate containing dicarboxylic acid;
e) evaporating liquid from the nanofiltered permeate of step d) to increase the concentration of dicarboxylic acid to minimally about 30 weight percent, and cooling to crystallize dicarboxylic acid; and
f) separating and drying crystalline dicarboxylic acid.

2. The process of claim 1, wherein the time which passes between removal of the fermentation broth from the fermenter and removal from the separating step a)1) does not exceed 2 hours.

3. The process of claim 1, wherein the time which passes between removal of the fermentation broth from the fermenter and removal from the separating step a)1) is less than 2 hours.

4. The process of claim 1, wherein the ultrafiltration unit of step a)2) has a single- or dual-stage membrane with a cut-off of ≤10 kDa, and wherein a brine which does not form the permeate is recycled to step a)1).

5. The process of claim 1, wherein the pH in step b) is lowered to a pH in the range of 2.2 to 2.4.

6. The process of claim 5, wherein the pH is lowered by addition of sulfuric acid.

7. The process of claim 5, wherein the temperature of the acidified permeate is maintained at a temperature in the range of 30° C. to 60° C.

8. The process of claim 5, wherein the temperature of the acidified permeate is maintained at a temperature in the range of 40° C. to 60° C.

9. The process of claim 5, wherein in step c), an eluent is added to the simulated moving-bed chromatography unit which removes bound dicarboxylic acid, the eluent supplied at a permeate to eluent ratio of 1:1.5 to 1:2.5.

10. The process of claim 9, wherein the dicarboxylic acid recovery is ≥95% relative to the amount of dicarboxylic acid contained in the permeate of step a)2).

11. The process of claim 5, wherein the cut-off of the nanofiltration unit of step d) is 200 Da.

12. The process of claim 1, wherein the nanofiltered permeate from step (d) is purified by contacting the nanofiltered permeate with activated carbon and/or further ion exchange resins to form a further permeate that is subsequently subjected to evaporation (step e).

13. The process of claim 5, wherein the cooling during crystallization in step (f) is conducted in steps of 3-8° C./min, and technical grade dicarboxylic acid with a dicarboxylic acid content of ≥97 weight percent is produced.

14. The process of claim 5, wherein the cooling during crystallization in step (f) is conducted in steps of 3-5° C./min, and technical grade dicarboxylic acid with a dicarboxylic acid content of ≥97 weight percent is produced.

15. The process of claim 5, wherein in step f), the temperature of the liquid is adjusted to between 70° C. to 80° C., and is evaporated until a concentration of 50±5 weight percent of dicarboxylic acid is obtained, cooling then takes place at a rate of 1-5° C./hour, and a polymer-grade dicarboxylic acid having a dicarboxylic acid content of ≥99.5 weight % is obtained.

16. The process of claim 5, wherein a mother liquor obtained following separation of crystalline dicarboxylic acid in step g) is recycled to step f).

17. The process of claim 5, wherein a brine from step a)2) and a brine from step d) are combined and used as a feedstock for production of technical grade dicarboxylic acid.

18. The process of claim 5, wherein the dicarboxylic acid comprises fumaric acid, maleic acid, adipic acid, itaconic acid, or succinic acid.

19. The process of claim 5, wherein the dicarboxylic acid is succinic acid.

20. The process of claim 1, wherein the nanofiltration of step (d) is conducted by means of nanofiltration unit containing a membrane having a maximum molecular weight cut-off of from 100 to 400 Da.

* * * * *